United States Patent
Roy et al.

(10) Patent No.: US 8,968,309 B2
(45) Date of Patent: Mar. 3, 2015

(54) SURGICAL FORCEPS

(75) Inventors: Jeffrey M. Roy, Boulder, CO (US);
Rebecca J. Coulson, Lyons, CO (US);
Sara E. Anderson, Erie, CO (US);
Robert M. Sharp, Boulder, CO (US)

(73) Assignee: Covidien LP, Mansfield, MA (US)

( * ) Notice: Subject to any disclaimer, the term of this patent is extended or adjusted under 35 U.S.C. 154(b) by 677 days.

(21) Appl. No.: 13/293,754

(22) Filed: Nov. 10, 2011

(65) Prior Publication Data

US 2013/0123837 A1    May 16, 2013

(51) Int. Cl.
*A61B 17/28*    (2006.01)
*A61B 18/14*    (2006.01)
*A61B 18/00*    (2006.01)

(52) U.S. Cl.
CPC .......... *A61B 18/1442* (2013.01); *A61B 18/1445* (2013.01); *A61B 2018/00607* (2013.01); *A61B 2018/1455* (2013.01); *A61B 2018/00428* (2013.01); *A61B 2018/1412* (2013.01); *A61B 2018/146* (2013.01)
USPC ............................................ 606/51; 606/205

(58) Field of Classification Search
None
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,431,674 A | 7/1995 | Basile et al. |
| D384,413 S | 9/1997 | Zlock et al. |
| H1745 H | 8/1998 | Paraschac |

(Continued)

FOREIGN PATENT DOCUMENTS

| | | |
|---|---|---|
| CN | 201299462 | 9/2009 |
| DE | 2415263 A1 | 10/1975 |

(Continued)

OTHER PUBLICATIONS

U.S. Appl. No. 08/926,869, James G. Chandler.

(Continued)

*Primary Examiner* — Brian T Gedeon
*Assistant Examiner* — Ankit Tejani

(57) ABSTRACT

An end effector of a forceps includes first and second jaw members movable between spaced-apart and approximated positions for grasping tissue. Each jaw member includes a tissue sealing plate that is selectively energizable. The tissue sealing plates are configured to conduct energy therebetween and though tissue to seal tissue. A knife includes a distal surface and an upper surface. The knife is selectively translatable between a retracted position and an extended position wherein the knife extends between the jaw members. The distal surface is configured for dynamic tissue cutting upon translation of the knife from the retracted to the extended position. The upper surface is configured for static tissue cutting with the knife in the extended position. The knife is selectively energizable and is configured to conduct energy between the knife and one or both of the tissue sealing plates and through tissue to electrically cut tissue.

20 Claims, 6 Drawing Sheets

(56) References Cited

U.S. PATENT DOCUMENTS

| | | |
|---|---|---|
| D402,028 S | 12/1998 | Grimm et al. |
| D408,018 S | 4/1999 | McNaughton |
| D416,089 S | 11/1999 | Barton et al. |
| 6,004,335 A | 12/1999 | Vaitekunas et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinge |
| D541,938 S | 5/2007 | Kerr et al |
| D545,432 S | 6/2007 | Watanabe |
| D547,154 S | 7/2007 | Lee et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 7,951,150 B2 | 5/2011 | Johnson et al. |
| D649,249 S | 11/2011 | Guerra |
| D649,643 S | 11/2011 | Allen, Iv et al. |
| D661,394 S | 6/2012 | Romero et al. |
| 2003/0078577 A1* | 4/2003 | Truckai et al. .......... 606/51 |
| 2007/0118111 A1 | 5/2007 | Weinberg |
| 2008/0039835 A1 | 2/2008 | Johnson et al. |
| 2008/0319442 A1 | 12/2008 | Unger et al. |
| 2010/0137854 A1 | 6/2010 | Hosier |
| 2010/0179545 A1* | 7/2010 | Twomey et al. ......... 606/51 |
| 2011/0004210 A1 | 1/2011 | Johnson et al. |
| 2011/0046623 A1 | 2/2011 | Reschke |
| 2011/0054467 A1 | 3/2011 | Mueller et al. |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1159926 A3 | 3/2003 |
| EP | 1769765 | 4/2007 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 9-122138 A | 5/1997 |
| JP | 0010000195 A | 1/1998 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-253789 A | 9/2005 |
| JP | 2006-015078 A | 1/2006 |
| JP | 2006-501939 A | 1/2006 |
| JP | 2006-095316 A | 4/2006 |
| JP | 2011125195 A | 6/2011 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 01/28444 A1 | 4/2001 |
| WO | 0154604 A1 | 8/2001 |
| WO | 02045589 A3 | 9/2002 |
| WO | 2006/021269 A1 | 3/2006 |
| WO | 2005110264 A3 | 4/2006 |
| WO | 2008/040483 A1 | 4/2008 |

OTHER PUBLICATIONS

U.S. Appl. No. 09/177,950, Randel A. Frazier.
U.S. Appl. No. 09/387,883, Dale F. Schmaltz.
U.S. Appl. No. 09/591,328, Thomas P. Ryan.
U.S. Appl. No. 12/336,970, Paul R. Sremeich.
U.S. Appl. No. 13/050,182, Glenn A. Horner.
U.S. Appl. No. 13/072,945, Patrick L. Dumbauld.
U.S. Appl. No. 13/080,383, David M. Garrison.
U.S. Appl. No. 13/085,144, Keir Hart.

(56) References Cited

OTHER PUBLICATIONS

U.S. Appl. No. 13/091,331, Jeffrey R. Townsend.
U.S. Appl. No. 13/102,573, John R. Twomey.
U.S. Appl. No. 13/102,604, Paul E. Ourada.
U.S. Appl. No. 13/108,093, Boris Chernov.
U.S. Appl. No. 13/108,129, Boris Chernov.
U.S. Appl. No. 13/108,152, Boris Chernov.
U.S. Appl. No. 13/108,177, Boris Chernov.
U.S. Appl. No. 13/108,196, Boris Chernov.
U.S. Appl. No. 13/108,441, Boris Chernov.
U.S. Appl. No. 13/108,468, Boris Chernov.
U.S. Appl. No. 13/111,642, John R. Twomey.
U.S. Appl. No. 13/111,678, Nikolay Kharin.
U.S. Appl. No. 13/113,231, David M. Garrison.
U.S. Appl. No. 13/157,047, John R. Twomey.
U.S. Appl. No. 13/162,814, Barbara R. Tyrrell.
U.S. Appl. No. 13/166,477, Daniel A. Joseph.
U.S. Appl. No. 13/166,497, Daniel A. Joseph.
U.S. Appl. No. 13/179,919, Russell D. Hempstead.
U.S. Appl. No. 13/179,960, Boris Chernov.
U.S. Appl. No. 13/179,975, Grant T. Sims.
U.S. Appl. No. 13/180,018, Chase Collings.
U.S. Appl. No. 13/183,856, John R. Twomey.
U.S. Appl. No. 13/185,593, James D. Allen, IV.
U.S. Appl. No. 13/204,841, Edward J. Chojin.
U.S. Appl. No. 13/205,999, Jeffrey R. Unger.
U.S. Appl. No. 13/212,297, Allan J. Evans.
U.S. Appl. No. 13/212,308, Allan J. Evans.
U.S. Appl. No. 13/212,329, Allan J. Evans.
U.S. Appl. No. 13/212,343, Duane E. Kerr.
U.S. Appl. No. 13/223,521, John R. Twomey.
U.S. Appl. No. 13/227,220, James D. Allen, IV.
U.S. Appl. No. 13/228,742, Duane E. Kerr.
U.S. Appl. No. 13/231,643, Keir Hart.
U.S. Appl. No. 13/234,357, James D. Allen, IV.
U.S. Appl. No. 13/236,168, James D. Allen, IV.
U.S. Appl. No. 13/236,271, Monte S. Fry.
U.S. Appl. No. 13/243,628, William Ross Whitney.
U.S. Appl. No. 13/247,778, John R. Twomey.
U.S. Appl. No. 13/247,795, John R. Tvvomey.
U.S. Appl. No. 13/248,976, James D. Allen, IV.
U.S. Appl. No. 13/249,013, Jeffrey R. Unger.
U.S. Appl. No. 13/249,024, John R. Twomey.
U.S. Appl. No. 13/251,380, Duane E. Kerr.
U.S. Appl. No. 13/277,373, Glenn A. Horner.
U.S. Appl. No. 13/277,926, David M. Garrison.
U.S. Appl. No. 13/277,962, David M. Garrison.
U.S. Appl. No. 13/293,754, Jeffrey M. Roy.
U.S. Appl. No. 13/306,523, David M. Garrison.
U.S. Appl. No. 13/306,553, Duane E. Kerr.
U.S. Appl. No. 13/308,104, John R. Twomey.
U.S. Appl. No. 13/312,172, Robert J. Behnke, II.
U.S. Appl. No. 13/324,863, William H. Nau, Jr.
U.S. Appl. No. 13/344,729, James D. Allen, IV.
U.S. Appl. No. 13/355,829, John R.Twomey.
U.S. Appl. No. 13/357,979, David M. Garrison.
U.S. Appl. No. 13/358,136, James D. Allen, IV.
U.S. Appl. No. 13/360,925, James H. Orszulak.
U.S. Appl. No. 13/400,290, Eric R. Larson.
U.S. Appl. No. 13/404,435, Kim V. Brandt.
U.S. Appl. No. 13/404,476, Kim V. Brandt.
U.S. Appl. No. 13/412,879, David M. Garrison.
U.S. Appl. No. 13/412,897, Joanna Ackley.
U.S. Appl. No. 13/421,373, John R. Tvvomey.
U.S. Appl. No. 13/430,325, William H. Nau, Jr.
U.S. Appl. No. 13/433,924, Keir Hart.
U.S. Appl. No. 13/448,577, David M. Garrison.
U.S. Appl. No. 13/460,455, Luke Waaler.
U.S. Appl. No. 13/461,335, James D. Allen, IV.
U.S. Appl. No. 13/461,378, James D. Allen, IV.
U.S. Appl. No. 13/461,397, James R. Unger.
U.S. Appl. No. 13/461,410, James R. Twomey.
U.S. Appl. No. 13/464,569, Duane E. Kerr.
U.S. Appl. No. 13/466,274, Stephen M. Kendrick.
U.S. Appl. No. 13/467,767, Duane E. Kerr.
U.S. Appl. No. 13/470,543, Sean T. Dycus.
U.S. Appl. No. 13/470,775, James D. Allen, IV.
U.S. Appl. No. 13/470,797, John J. Kappus.
U.S. Appl. No. 13/482,589, Eric R. Larson.
U.S. Appl. No. 13/483,733, Dennis W. Butcher.
U.S. Appl. No. 13/488,093, Kristin D. Johnson.
U.S. Appl. No. 13/491,853, Jessica E. Olson.
U.S. Appl. No. 13/537,517, David N. Heard.
U.S. Appl. No. 13/537,577, Tony Moua.
U.S. Appl. No. 13/550,322, John J. Kappus.
U.S. Appl. No. 13/571,055, Paul Guerra.
U.S. Appl. No. 13/571,821, Joseph D. Bucciaglia.
U.S. Appl. No. 13/584,194, Sean T. Dycus.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hennorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1967), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.

(56) References Cited

OTHER PUBLICATIONS

Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
European Search Report from corresponding application EP 12191975 dated Jan. 31, 2013.

* cited by examiner

SURGICAL FORCEPS

BACKGROUND

1. Technical Field

The present disclosure relates to surgical instruments and, more particularly, to surgical forceps for grasping, sealing and/or dissecting tissue.

2. Background of Related Art

A forceps is a plier-like instrument which relies on mechanical action between its jaws to grasp, clamp and constrict vessels or tissue. Electrosurgical forceps utilize both mechanical clamping action and electrical energy to affect hemostasis by heating tissue and blood vessels to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles.

Typically, once a vessel is sealed, the surgeon has to accurately sever the vessel along the newly formed tissue seal. Accordingly, many vessel sealing instruments have been designed which incorporate a knife or blade member that effectively severs the tissue after forming a tissue seal. In certain instances, it may be necessary to dissect, or cut through tissue in order to reach an underlying vessel (or vessels), or for other purposes.

SUMMARY

As used herein, the term "distal" refers to the portion that is being described which is further from a user, while the term "proximal" refers to the portion that is being described which is closer to a user. The terms "knife" and "tissue-cutting surface," as used herein, do not necessarily mean a component, or portion thereof, that includes a sharp cutting edge for mechanical cutting. Rather, "knife" and "tissue-cutting surface" are used herein to more generally refer to those components, or portions thereof, that are used to cut tissue, e.g., a blunt component or surface for electrical tissue cutting, an edge or corner to facilitate electrical tissue cutting, a sharpened component or surface for mechanical tissue cutting, or combinations thereof.

Any of the aspects described herein, to the extent consistent, may be used in conjunction with any of the other aspects described herein.

In accordance with one aspect of the present disclosure, a forceps is provided. The forceps includes an end effector assembly having first and second jaw members. One or both of the jaw members is movable relative to the other between a spaced-apart position and an approximated position for grasping tissue therebetween. Each jaw member includes an electrically-conductive tissue sealing plate that is adapted to connect to a source of energy. The tissue sealing plates are selectively energizable independently of one another and are configured to conduct energy therebetween and though tissue to seal tissue. A knife includes a distal tissue-cutting surface and an upper tissue-cutting surface. The knife is selectively translatable relative to the jaw members between a retracted position and an extended position, wherein the knife extends between the jaw members. The distal tissue-cutting surface is configured for dynamic tissue cutting upon translation of the knife from the retracted position to the extended position. The upper tissue-cutting surface is configured for static tissue cutting when the knife is disposed in the extended position. The knife is adapted to connect to the source of energy and is selectively energizable independently of the tissue sealing plates. The knife is configured to conduct energy between the knife and one or both of the tissue sealing plates and through tissue to electrically cut tissue.

In one aspect, a handle assembly is provided for selectively moving the jaw members between the spaced-apart and approximated positions.

In another aspect, a trigger assembly is provided for selectively translating the knife between the retracted and extended positions.

In another aspect, a first activation switch is provided for selectively energizing the tissue sealing plate of the first jaw member and a second activation switch is provided for selectively energizing the tissue sealing plate of the second jaw member.

In yet another aspect, a knife actuation switch is provided for selectively energizing the knife.

In still another aspect, the knife and the tissue sealing plates of the first and second jaw members are energizable to conduct energy therebetween and through tissue to electrically cut tissue when the knife is translated between the retracted and extended positions.

In still yet another aspect, the knife and the tissue sealing plate of the second jaw member are energizable to conduct energy therebetween and through tissue to electrically cut tissue via tenting when the jaw members are disposed in the spaced-apart position and the knife is disposed in the extended position.

In another aspect, the knife and the tissue sealing plate of the first jaw member are energizable to conduct energy therebetween and through tissue to electrically cut tissue via scissor-cutting.

In another aspect, one or more insulators are disposed between the knife and the tissue sealing plates. The insulators are configured to inhibit contact between the knife and the tissue sealing plates.

A method of surgery is also provided in accordance with the present disclosure. The method includes providing a forceps having an end effector assembly including first and second jaw members. Each jaw member includes an electrically-conductive tissue sealing plate adapted to connect to a source of energy. A knife is selectively translatable between the first and second jaw members. The method further includes moving the jaw members to an approximated position relative to one another to grasp tissue therebetween, energizing the tissue sealing plate of one (or both) of the first and second jaw members to seal tissue grasped between the jaw members, moving the jaw members to a spaced-apart position relative to one another, deploying the knife between the jaw members, overlaying the tissue seal across an upper edge of the knife, and moving the end effector assembly transversely relative to tissue to cut tissue via tenting.

In one aspect, the knife is adapted to connect to the source of energy. In such an aspect, the knife may be energized to electrically cut tissue via tenting. The forceps may further include a knife actuation switch for selectively energizing the knife.

In another aspect, the forceps includes a trigger assembly for selectively deploying the knife between the jaw members, e.g., for translating the knife between a retracted position and an extended position.

In yet another aspect, the forceps includes a handle assembly for moving the jaw members between the spaced-apart position and the approximated position.

In still another aspect, the forceps includes a first activation switch for selectively energizing the tissue sealing plate of the first jaw member and a second activation switch for selectively energizing the tissue sealing plate of the second jaw member.

A method of surgery provided in accordance with another aspect of the present disclosure includes providing a forceps according to any of the above aspects. The method further includes moving the jaw members to an approximated position relative to one another to grasp tissue therebetween, energizing the tissue sealing plate of one (or both) of the first and second jaw members to seal tissue grasped between the jaw members, opening the jaw members relative to one another, deploying the knife between the jaw members, positioning the tissue seal between the jaw members, and moving the jaw members from the spaced-apart position to the approximated position to scissor-cut tissue along the tissue seal.

In one aspect, the knife is adapted to connect to the source of energy. In such an aspect, the knife may be energized to electrically scissor-cut tissue. The forceps may further include a knife actuation switch for selectively energizing the knife.

BRIEF DESCRIPTION OF THE DRAWINGS

Various aspects of the present disclosure are described in detail with reference to the drawing figures wherein like reference numerals identify similar or identical elements.

DETAILED DESCRIPTION

Figure 1:
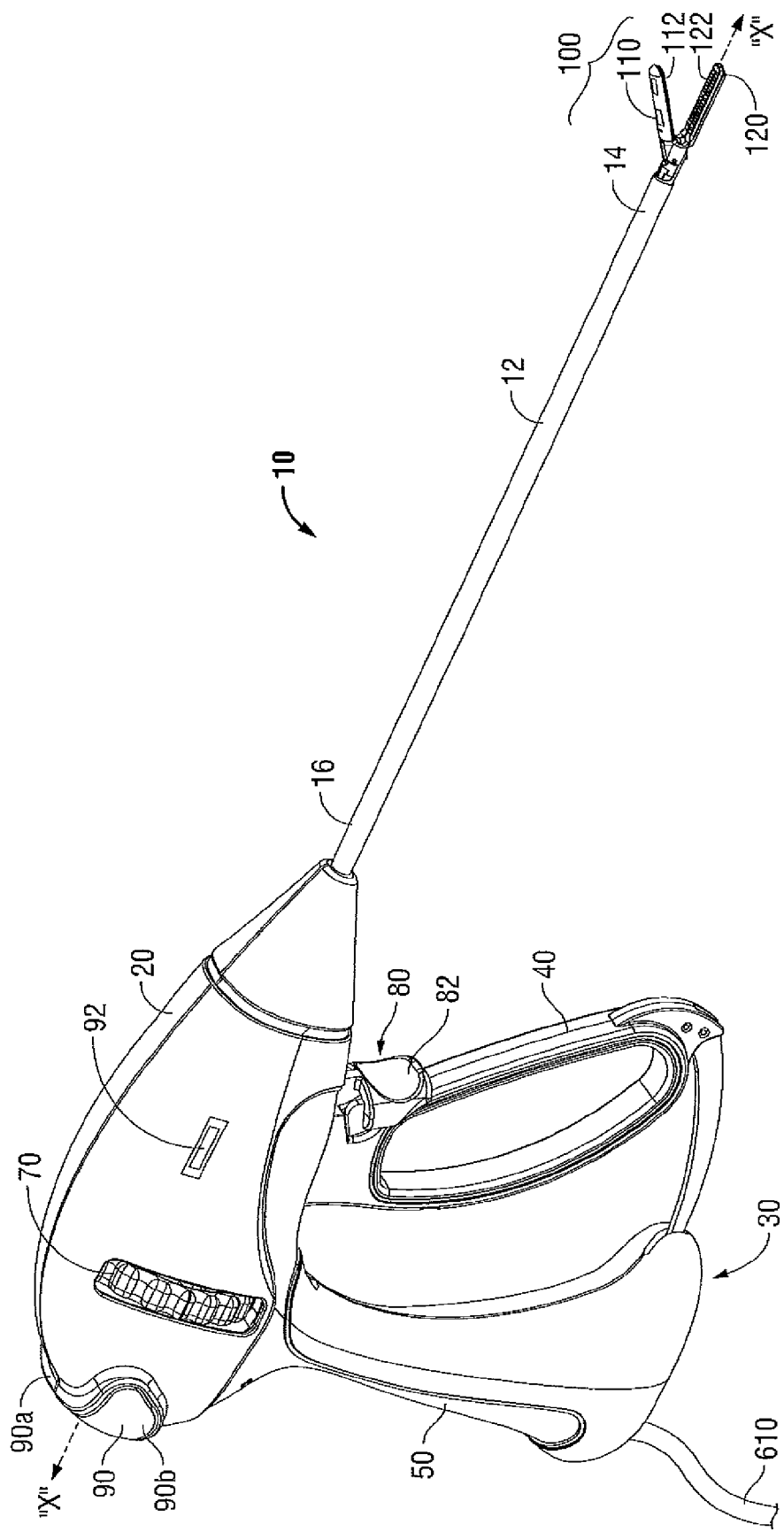
FIG. 1 is a front, perspective view of an endoscopic surgical forceps configured for use in accordance with the present disclosure.
Figure 2:
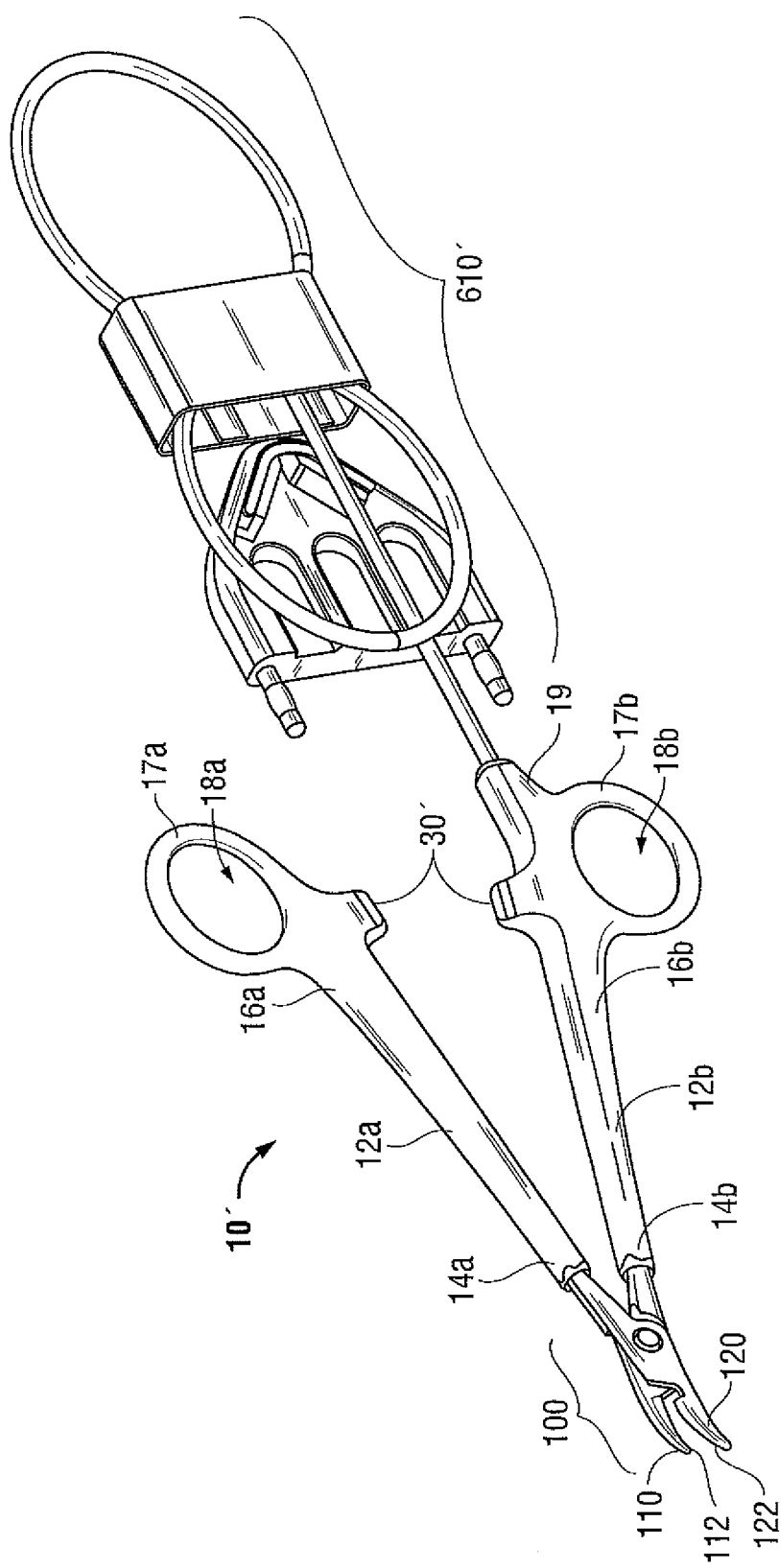
FIG. 2 is a front, perspective view of an open surgical forceps configured for use in accordance with the present disclosure.

Referring now to FIGS. 1 and 2, FIG. 1 depicts a forceps 10 for use in connection with endoscopic surgical procedures and FIG. 2 depicts an open forceps 10' contemplated for use in connection with traditional open surgical procedures. For the purposes herein, either an endoscopic instrument, e.g., forceps 10, or an open instrument, e.g., forceps 10', may be utilized in accordance with the present disclosure. Obviously, different electrical and mechanical connections and considerations apply to each particular type of instrument; however, the novel aspects with respect to the end effector assembly and its operating characteristics remain generally consistent with respect to both the open and endoscopic configurations.

Turning now to FIG. 1, an endoscopic forceps 10 is provided defining a longitudinal axis "X-X" and including a housing 20, a handle assembly 30, a rotating assembly 70, a trigger assembly 80, and an end effector assembly 100. Forceps 10 further includes a shaft 12 having a distal end 14 configured to mechanically engage end effector assembly 100 and a proximal end 16 that mechanically engages housing 20. Forceps 10 also includes electrosurgical cable 610 that connects forceps 10 to a generator (not shown) or other suitable power source, although forceps 10 may alternatively be configured as a battery powered instrument. Cable 610 includes wires (not shown) extending therethrough that has sufficient length to extend through shaft 12 in order to provide electrical energy to at least one of the sealing plates 112, 122 of jaw members 110, 120, respectively, of end effector assembly 100, e.g., upon activation of activation switch 90.

With continued reference to FIG. 1, handle assembly 30 includes a fixed handle 50 and a moveable handle 40. Fixed handle 50 is integrally associated with housing 20 and moveable handle 40 is moveable relative to fixed handle 50. Rotating assembly 70 is rotatable in either direction about longitudinal axis "X-X" to rotate end effector 100 about longitudinal axis "X-X." Housing 20 houses the internal working components of forceps 10.

End effector assembly 100 is shown attached at a distal end 14 of shaft 12 and includes a pair of opposing jaw members 110, 120. Each of the jaw members 110, 120 includes an electrically-conductive tissue sealing plate 112, 122, respectively. End effector assembly 100 is designed as a unilateral assembly, e.g., where jaw member 120 is fixed relative to shaft 12 and jaw member 110 is moveable relative to shaft 12 and fixed jaw member 120 (although the reverse configuration is also contemplated). However, end effector assembly 100 may alternatively be configured as a bilateral assembly, i.e., where both jaw member 110 and jaw member 120 are moveable relative to one another and to shaft 12. A knife assembly 180 (FIGS. 4-5C) is disposed within shaft 12 and a knife channel 115, 125 (FIGS. 5A-5C) is defined within one or both jaw members 110, 120 to permit reciprocation of a knife 184 (FIGS. 4-5C) therethrough, e.g., via actuation of a trigger 82 of trigger assembly 80. The particular features of end effector assembly 100 and knife assembly 180 (FIGS. 4-50) will be described in greater detail hereinbelow.

Continuing with reference to FIG. 1, moveable handle 40 of handle assembly 30 is ultimately connected to a drive assembly (not shown) that, together, mechanically cooperate to impart movement of jaw members 110, 120 between a spaced-apart position and an approximated position to grasp tissue disposed between sealing plates 112, 122 of jaw members 110, 120, respectively. As shown in FIG. 1, moveable handle 40 is initially spaced-apart from fixed handle 50 and, correspondingly, jaw members 110, 120 are in the spaced-apart position. Moveable handle 40 is movable from this initial position to a depressed position to move jaw members 110, 120 to the approximated position for grasping tissue therebetween (see FIGS. 5B-5C).

Referring now to FIG. 2, an open forceps 10' is shown including two elongated shafts 12a, 12b, each having a proximal end 16a, 16b and a distal end 14a, 14b, respectively. Similar to forceps 10 (FIG. 1), forceps 10' is configured for use with end effector assembly 100. More specifically, end effector assembly 100 is attached to distal ends 14a, 14b of shafts 12a, 12b, respectively. As mentioned above, end effector assembly 100 includes a pair of opposing jaw members 110, 120 that are pivotably coupled to one another. Each shaft 12a, 12b includes a handle 17a, 17b disposed at the proximal end 16a, 16b thereof. Each handle 17a, 17b defines a finger hole 18a, 18b therethrough for receiving a finger of the user. As can be appreciated, finger holes 18a, 18b facilitate movement of shafts 12a, 12b relative to one another which, in turn, pivots jaw members 110, 120 from an open position, wherein jaw members 110, 120 are disposed in spaced-apart relation relative to one another, to a closed position, wherein jaw members 110, 120 cooperate to grasp tissue therebetween.

A ratchet 30' may be included for selectively locking jaw members 110, 120 relative to one another at various positions during pivoting. Ratchet 30' may include graduations or other visual markings that enable the user to easily and quickly ascertain and control the amount of closure force desired between jaw members 110, 120.

With continued reference to FIG. 2, one of the shafts, e.g., shaft 12b, includes a proximal shaft connector 19 that is designed to connect forceps 10' to a source of electrical energy such as an electrosurgical generator (not shown). Proximal shaft connector 19 secures an electrosurgical cable 610' to forceps 10' such that the user may selectively apply electrosurgical energy to electrically-conductive tissue sealing plates 112, 122 of jaw members 110 and 120, respectively, as needed.

Forceps 10' may further include a knife assembly 180 (FIGS. 4-5C) disposed within either of shafts 12a, 12b and a knife channel 115, 125 (FIGS. 5A-5C) defined within one or both of jaw members 110, 120, respectively, to permit reciprocation of a knife 184 (FIGS. 5-8C) therethrough.

Figure 3:
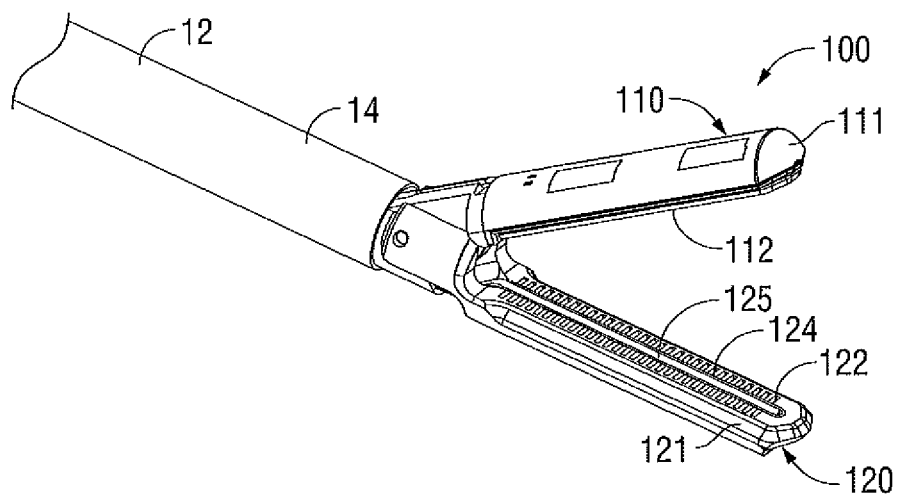
FIG. 3 is an enlarged, front, perspective view of an end effector assembly configured for use with the forceps of FIG. 1 or 2.

Turning now to FIG. 3, end effector assembly 100, including jaw members 110, 120 is configured for use with either forceps 10 or forceps 10', discussed above, or any other suitable surgical instrument capable of pivoting jaw members 110, 120 relative to one another between a spaced-apart position and an approximated position for grasping tissue therebetween. However, for purposes of simplicity and consistency, end effector assembly 100 will be described hereinbelow with reference to forceps 10 only.

Jaw members 110, 120, as shown in FIG. 3, each include an outer, insulative jaw housing 111, 121 and an electrically-conductive tissue sealing plate 112, 122 disposed atop respective jaw housings 111, 121 in opposed relation relative to one another. Tissue sealing plates 112, 122 are adapted to connect to a source of electrical energy, e.g., electrosurgical energy, independently of one another such that, as will be described in detail below, either or both of tissue sealing plates 112, 122 may be selectively energized, depending on a particular purpose. Activation switch 90 (FIG. 1) is selectively actuatable to control the supply of energy to tissue sealing plates 112, 122. More specifically, activation switch 90 (FIG. 1) may include first and second switch components 90a, 90b (FIG. 1) to facilitate selective activation of either or both of tissue sealing plates 112, 122.

One or both of jaw members 110, 120 includes a longitudinally-extending knife channel 115, 125 (FIGS. 5A-5C) that, as mentioned above, is configured to permit reciprocation of a knife 184 (FIGS. 4-5C) therethrough. An insulator 124 lines each of knife channels 115, 125 to electrically isolate knife 184 (FIG. 4) from tissue sealing plates 112, 122.

Figure 4:
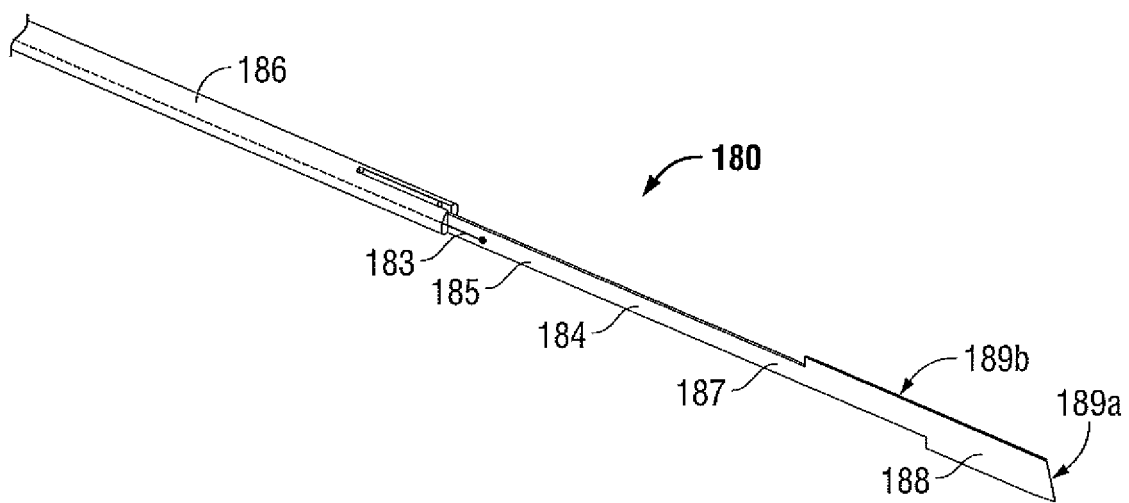
FIG. 4 is a perspective view of a knife assembly configured for use with the forceps of FIG. 1 or 2.
Figure 5A:
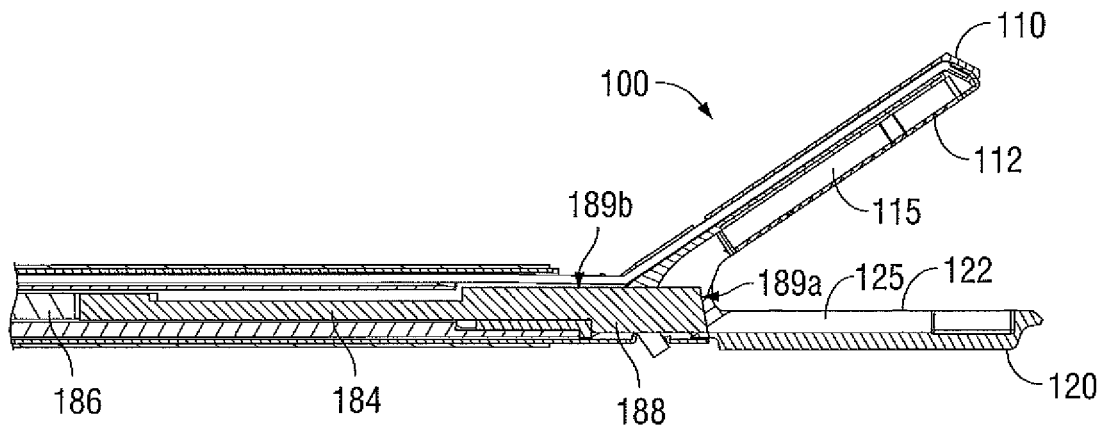
FIG. 5A is a longitudinal, cross-sectional view of the end effector assembly of FIG. 3, wherein the jaw members are shown in a spaced-apart position and wherein the knife assembly is shown in a retracted position.

Turning now to FIG. 4, knife assembly 180 generally includes a knife 184 and a knife bar 186. Knife 184 is coupled to a knife bar 186 at the proximal end 185 of knife 184 and extends distally from knife bar 186 to define a tissue-cutting portion 188 at the distal end 187 thereof. Tissue-cutting portion 188 of knife 184 defines both a distal tissue-cutting surface 189a to facilitate cutting of tissue as knife 184 is translated longitudinally relative to tissue and an upper tissue-cutting surface 189b extending along the length of tissue-cutting portion 188 to facilitate cutting of tissue as knife 184 is translated transversely relative to tissue. Tissue-cutting surfaces 189a, 189b may define sharpened-blade configurations, dull-blade configurations, blunt configurations, or combinations thereof (e.g., distal tissue-cutting surface 189a may define a sharpened-blade, while upper tissue-cutting surface 189b defines a blunt configuration, although the reverse configuration or other configurations are also contemplated). Further, tissue-cutting surfaces 189a, 189b may define various different edge or corner configurations to concentrate electrical current and facilitate electrical cutting of tissue.

With continued reference to FIG. 4, knife 184 is coupled to a source of energy, e.g., electrosurgical energy, via lead wire 183. Lead wire 183 extends from knife 184 proximally through shaft 12 (FIG. 1), ultimately coupling to a source of energy, e.g., to a portable generator (not shown) disposed within housing 20 (for battery-powered instruments), or to an external generator (not shown) via cable 610 (FIG. 1). A knife activation switch 92 (FIG. 1) disposed on housing 20 (FIG. 1) is selectively activatable to energize knife 184, e.g., to control the supply of energy from lead wire 183 to knife 184.

Turning now to FIGS. 1, 3, and 5A-7B, end effector assembly 100 is configured to operate in various different modes and to transition efficiently between the various different modes of operation. As such, end effector assembly 100 is capable of performing a variety of surgical tasks without requiring the use of additional instrumentation and without requiring withdrawal of end effector assembly 100 to transition end effector assembly 100 to a different mode of operation. In particular, end effector assembly 100 is configured at least for: grasping tissue between jaw members 110, 120; sealing tissue grasped between jaw members 110, 120; mechanically cutting tissue grasped between jaw members 110, 120; electrically/electromechanically cutting tissue grasped between jaw members 110, 120; mechanically cutting tissue with jaw members 110, 120 disposed in the spaced-apart position; electrically/electromechanically cutting tissue with jaw members 110, 120 disposed in the spaced-apart position; mechanically scissor-cutting tissue; and electrically/electromechanically scissor-cutting tissue. Each mode of operation is described in detail below.

Figure 5B:
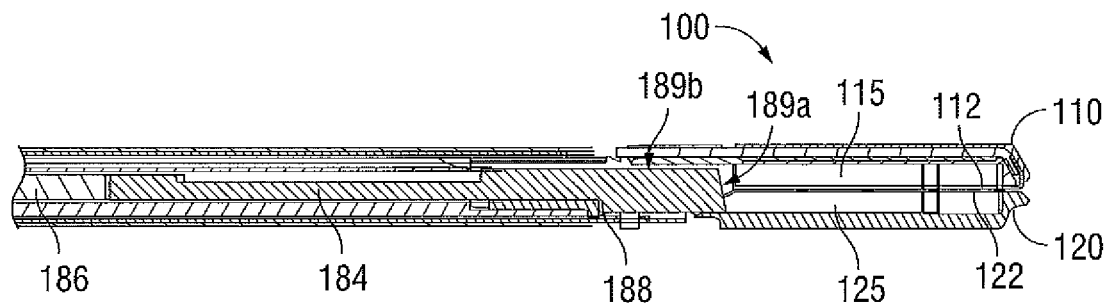
FIG. 5B is a longitudinal, cross-sectional view of the end effector assembly of FIG. 3, wherein the jaw members are shown in an approximated position and wherein the knife assembly is shown in the retracted position.
Figure 5C:
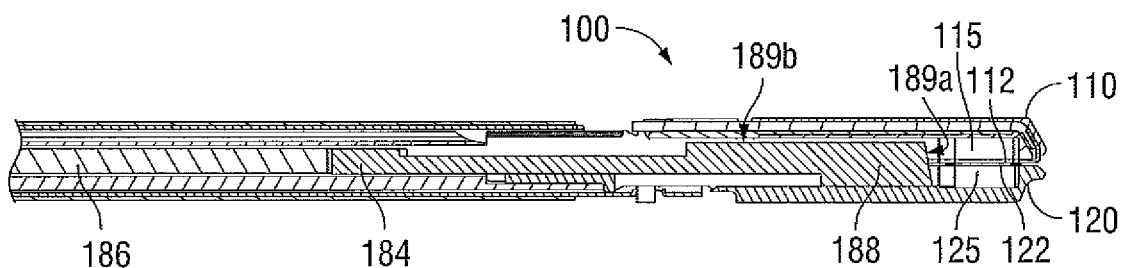
FIG. 5C is a longitudinal, cross-sectional view of the end effector assembly of FIG. 3, wherein the jaw members are shown in an approximated position and wherein the knife assembly is shown in an extended position.

Referring to FIGS. 1, 3 and 5A-5C, the use of end effector assembly 100 for grasping, sealing, and/or cutting tissue, e.g., mechanically, electrically, or electromechanically cutting tissue, grasped between jaw members 110, 120 is described. Initially, with jaw members 110, 120 disposed in the spaced-apart position (FIG. 5A), end effector assembly 100 is maneuvered into position such that tissue to be grasped, sealed, and/or cut is disposed between jaw members 110, 120. Next, moveable handle 40 is pulled proximally relative to fixed handle 50 such that jaw member 110 is pivoted relative to jaw member 120 from the spaced-apart position to the approximated position to grasp tissue between tissue sealing plates 112, 122 of jaw members 110, 120, respectively (FIG. 5B). Thereafter, energy may be supplied, e.g., via activation of activation switch 90 to tissue sealing plate 112 and/or tissue sealing plate 122 and conducted through tissue to effect a tissue seal. For example, tissue sealing plate 112 of jaw member 110 may be energized to a first potential, e.g., via activation of first switch component 90a, while tissue sealing plate 122 of jaw member 120 is energized to a second potential different from the first (or is not energized), e.g., via activation of second switch component 90b, thus creating a potential difference between tissue sealing plates 112, 122 such that energy is conducted therebetween and through tissue to effect a tissue seal. That is, in this configuration, tissue sealing plate 112 functions as the "active" electrode, while tissue sealing plate 122 functions as the "return" electrode. Other configurations for sealing tissue are also contemplated, e.g., wherein tissue sealing plate 122 is the "active" electrode and wherein tissue sealing plate 112 is the "return" electrode.

Once tissue sealing is complete (or where only grasping and cutting is desired), knife 184 may be advanced from the retracted position (FIG. 5B) to the extended position (FIG. 5C), e.g., via activation of trigger 82, such that knife 184 is translated through knife channels 115, 125 of jaw members 110, 120, respectively, to cut tissue grasped between jaw members 110, 120. As knife 184 is translated distally though knife channels 115, 125 of jaw members 110, 120, respectively, distal tissue-cutting portion 189a of knife 184 mechanically cuts or dissects tissue grasped between jaw members 110, 120.

Continuing with reference to FIGS. 1, 3 and 5A-5C, knife 184 may be energized as knife 184 is advanced through jaw members 110, 120 to facilitate cutting of tissue. More specifically, knife activation switch 92 may be activated to supply energy to knife 184 (the "active" electrode), via lead wire 183 (FIG. 4), for electrically/electromechanically cutting tissue grasped between jaw members 110, 120. In this mode, tissue sealing plates 112, 122 are not energized (or are energized to a different potential from knife 184), thus functioning as the "return" electrode. In use, as the energized knife 184 is translated through jaw members 110, 120, energy is conducted between distal tissue-cutting surface 189a and tissue sealing plates 112, 122 and through tissue therebetween to electrically cut tissue, while the advancement of distal tissue-cutting surface 189a through tissue mechanically cuts tissue. This conduction of energy through tissue for electrical cutting also results in some coagulation of tissue adjacent the cut line. Insulators 124 lining knife channels 115, 125 of jaw members 110, 120, respectively, inhibit contact between knife 184 and tissue sealing plates 112, 122 as knife 184 is translated therethrough, thus inhibiting shorting of the electrodes.

The particular mode of end effector assembly 100, e.g., grasping, tissue sealing, mechanical tissue cutting, and/or electrical tissue cutting, used for sealing and/or dividing tissue, may depend on the size and/or composition of tissue, the procedure to be performed, other anatomical considerations, etc. For example, for certain tissue, e.g., more avascular tissue, or where rapid dissection is required, it may be sufficient to grasp tissue between jaw members 110, 120, energize knife 184, and advance knife 184 between jaw members to electrically cut tissue, while the coagulation adjacent the cut line sufficiently reduces bleeding. For other tissue, e.g., more vascular tissue, or where rapid dissection is not as important, tissue may be grasped and sealed prior to advancement of knife 184 to cut tissue along the tissue seal. In this mode, the size and/or composition of tissue, or other factors, may dictate whether mechanical cutting or electrical/electromechanical cutting is required.

With reference to FIGS. 1, 3 and 6A-6B, the use of end effector assembly 100 for open-jaw tissue cutting, e.g., wherein jaw members 110, 120 are disposed in the spaced-apart position, is described. As mentioned above, knife 184 includes an upper tissue-cutting surface 189b extending along the length of tissue-cutting portion 188 of knife 184. Thus, with jaw members 110, 120 disposed in the spaced-apart position and with knife 184 in the extended position, upper tissue-cutting surface 189b is exposed such that end effector assembly 100 may be advanced transversely through tissue to cut tissue using upper tissue-cutting surface 189b of knife 184.

In use, with jaw members 110, 120 disposed in the spaced-apart position, end effector assembly 100 is moved into positioned adjacent tissue to be cut. At this point, or prior to, knife 184 is advanced to the extended position, e.g., via activation of trigger 82 of trigger assembly 80. Knife 184 is retained in the extended position via maintaining trigger 82 in an activated, or depressed position, although trigger assembly 80 may also include a locking mechanism (not explicitly shown) for selectively locking knife 184 in the extended position. In the mechanical cutting mode, with knife 184 in the extended position, end effector assembly 100 is advanced transversely relative to tissue to mechanically cut tissue using upper tissue-cutting surface 189b of knife 184, as shown in FIG. 6B.

In the electrical/electromechanical cutting mode, knife 184 is energized during open-jaw tissue cutting to facilitate cutting of tissue. More specifically, knife activation switch 92 may be activated to supply energy to knife 184 (the "active" electrode) via lead wire 183 (FIG. 4) for electrically/electromechanically cutting tissue grasped between jaw members 110, 120. In this configuration, tissue sealing plate 112 is not energized. Tissue sealing plate 122 is energized to a different potential from that of knife 184, e.g., via activation of second switch component 90b, such that tissue sealing plate 122 functions as the "return" electrode. Insulator 124 lining knife channel 125 of jaw member 120 inhibits contact between knife 184 and tissue sealing plate 122, thus inhibiting shorting of the electrodes.

Figure 6A:
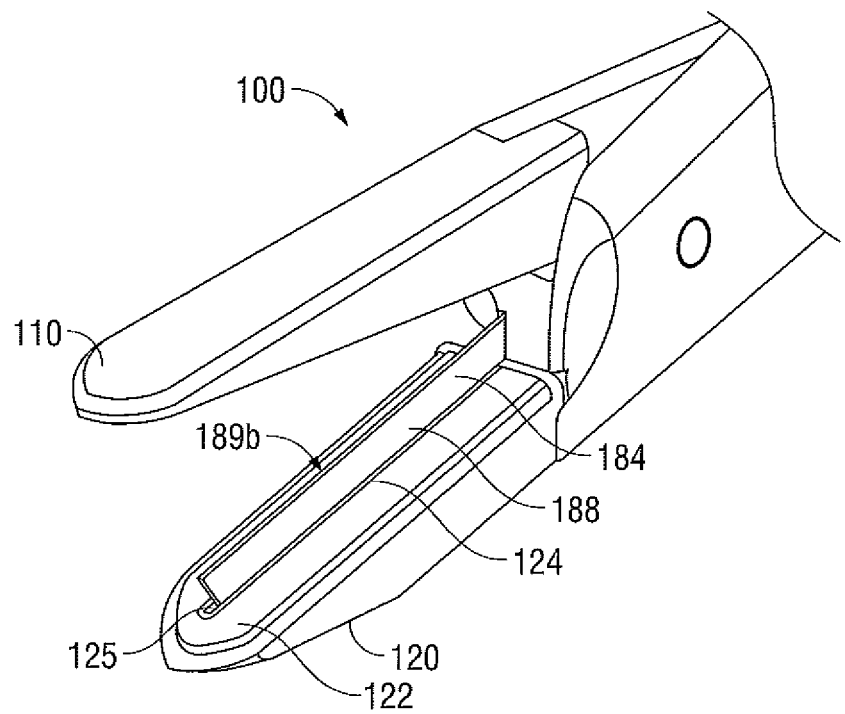
FIG. 6A is a front, perspective view of the end effector assembly of FIG. 3, wherein the jaw members are shown in the spaced-apart position and wherein the knife assembly is shown in the extended position.
Figure 6B:
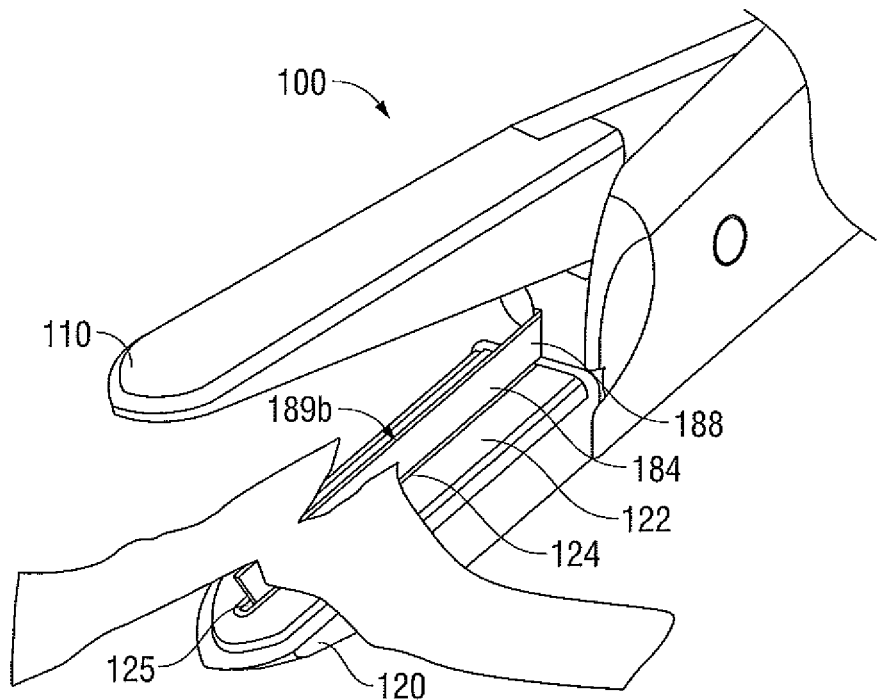
FIG. 6B is a front, perspective view of the end effector assembly of FIG. 3, wherein the jaw members are in the spaced-apart position and the knife assembly is in the extended position to dissect tissue.
Figure 7A:
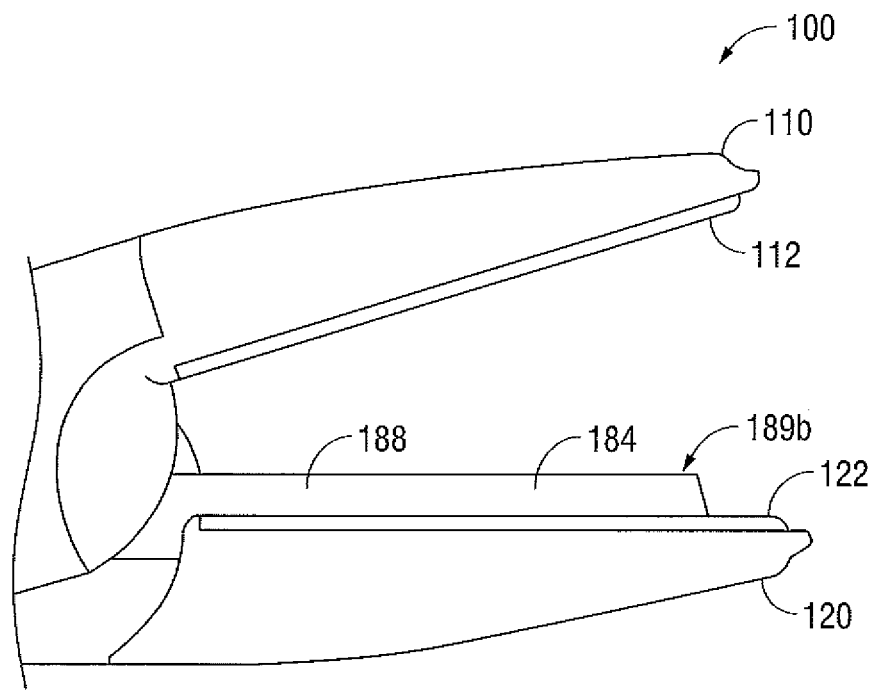
FIG. 7A is a side view of the end effector assembly of FIG. 3, wherein the jaw members are shown in the spaced-apart position and wherein the knife assembly is shown in the extended position.
Figure 7B:
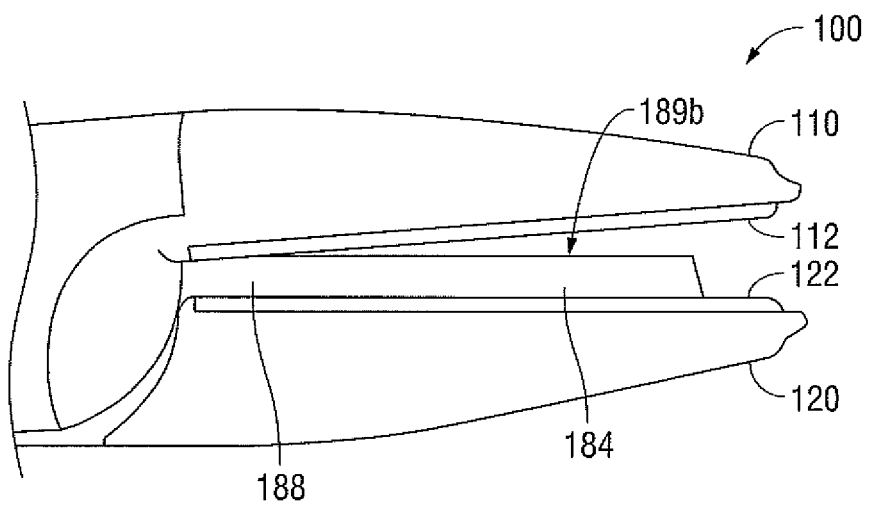
FIG. 7B is a side view of the end effector assembly of FIG. 3, wherein the jaw members are shown moving towards the approximated position and wherein the knife assembly is shown in the extended position.

Continuing with reference to FIGS. 1, 3 and 6A-6B, with knife 184 energized as the "active" electrode and with tissue sealing plate 122 energized as the "return" electrode, end effector assembly 100 may be advanced transversely through tissue to electrically/electromechanically cut tissue disposed between jaw members 110, 120 via tenting. Tenting, as shown in FIG. 6B, involves positioning end effector assembly 100 such that tissue to be cut lays over upper tissue-cutting surface 189b of knife 184 and extends toward jaw member 120 on either side of knife 184 to contact tissue sealing plate 122 of jaw member 120, thus forming a tent-like configuration. In this configuration, tissue contacts upper tissue-cutting surface 189b of knife 184 at the apex of the tent and tissue sealing plate 122 on the sides of the tent such that energy is conducted from knife 184, through tissue, to tissue sealing plate 122 to electrically cut tissue, while upper tissue-cutting surface 189b is advanced through tissue to mechanically cut tissue. The transverse translation of end effector assembly 100 relative to tissue during cutting, i.e., the urging of upper tissue-cutting surface 189b of knife 184 into tissue, helps maintain sufficient tension on tissue and helps ensure contact of tissue with tissue sealing plate 122 on either side of knife 184, thus facilitating the cutting of tissue as end effector assembly 100 is translated transversely therethrough.

It has been found that proper knife height is important in order to achieve optimal tenting. A knife height that is too small may not sufficiently tension tissue, making it more difficult to cut through tissue and insufficiently defining an energy path through tissue. On the other hand, a knife height that is too large may result in too much tenting, e.g., where tissue does not contact or does not sufficiently contact tissue sealing plate 122, reducing the effective current path through tissue between knife 184 and tissue sealing plate 122. Further, the sides of knife 184 may be coated with a dielectric, e.g., silicone, kapton, or any other suitable dielectric, to concentrate energy at upper tissue tissue-cutting surface 189b of knife 184, thus creating a more defined current path through tissue to tissue sealing plate 122 during cutting. This dielectric coating is also advantageous when end effector assembly 100 is used in the grasping and electrical/electromechanical tissue mode (see FIGS. 5A-5C) or the electrical/electromechanical scissor-cutting mode (see FIGS. 7A-7B), e.g., the dielectric coating facilitates the concentration of energy at the tissue-cutting surface (distal tissue-cutting surface 189a, for the grasping and electrical/electromechanical tissue mode, or upper tissue-cutting surface 189b, for the electrical/electromechanical scissor-cutting mode) of knife 184, thus creating a more defined current path through tissue.

The open-jaw tissue cutting mode (e.g., both the mechanical open-jaw cutting mode and the electrical/electromechanical open-jaw cutting mode) of end effector assembly 100 is particularly advantageous where rapid or repeated tissue cutting (without tissue sealing) is required, e.g., for providing access to underlying tissue. For example, the open-jaw tissue cutting mode allows end effector assembly 100 to continuously cut and advance through tissue (e.g., multiple layers of tissue) in order to efficiently and expediently access underlying tissue or an underlying surgical site. Certain tissue, e.g., smaller-diametered tissue, may be cut using mechanical cutting, while other tissue, e.g., stronger or larger tissue, may necessitate the use of tenting and electrical/electromechanical cutting.

With reference to FIGS. 1, 3 and 7A-7B, the use of end effector assembly 100 for mechanically or electro-mechanically scissor-cutting tissue is described. As mentioned above, knife 184 includes an upper tissue-cutting surface 189b extending along the length of tissue-cutting portion 188 of knife 184. Thus, with jaw members 110, 120 disposed in the spaced-apart position and with knife 184 in the extended position, upper tissue-cutting surface 189b is exposed. Accordingly, jaw members 110, 120 may be repeatedly moved between the spaced-apart and approximated positions in scissor-like fashion, e.g., via repeatedly squeezing and releasing moveable handle 40, to mechanically cut tissue disposed between jaw members 110, 120. More specifically, in use, tissue is positioned between jaw members 110, 120 such that, as jaw members 110, 120 are moved from the spaced-apart position to the approximated position, upper tissue-cutting surface 189b of knife 184 is translated through tissue positioned therebetween and into knife channel 115 (FIGS. 5A-5C) of jaw member 110 to cut tissue, while tissue is held in position between jaw members 110, 120.

With continued reference to FIGS. 1, 3 and 7A-7B, end effector assembly 100 may also be used to electromechanically scissor-cut tissue. For electromechanical scissor-cutting, knife 184 is energized, e.g., via activation of knife activation switch 92, to function as the "active" electrode, while tissue sealing plate 112 is energized to a different potential, e.g., via activation of first switch component 90a, such that tissue sealing plate 112 functions as the "return" electrode. In this configuration, tissue sealing plates 122 is not energized.

In use, in the electrical/electromechanical scissor-cutting mode, tissue is positioned between jaw members 110, 120 and jaw members 110, 120 are moved from the spaced-apart position to the approximated position. As jaw members 110, 120 are moved towards the approximated position, some mechanical cutting is achieved as upper tissue tissue-cutting surface 189b of knife 184 is urged into tissue positioned between knife 184 and knife channel 115 (FIGS. 5A-5C) of jaw member 110. As jaw members 110, 120 are moved further towards the approximated position, knife 184 and jaw members 110 urge tissue into contact with tissue sealing plate 122 of jaw member 120, to create a current path through tissue from upper tissue-cutting surface 189b of knife 184 to tissue sealing plate 122, thus allowing conduction of energy therebetween to electrically cut tissue.

The scissor-cutting mode (e.g., both the mechanical and electrical/electromechanical scissor-cutting mode) of end effector assembly 100 is particularly advantageous for cutting stronger and/or lager tissue in that jaw members 110, 120 retain tissue in position as knife 184 is advanced therethrough. The particular procedure, size and/or composition of tissue, or other factors may dictate whether mechanical cutting is sufficient or whether electrical/electromechanical cutting is necessary.

With reference to FIGS. 1-7B, as detailed above, end effector assembly 100 is configured for use in various modes of operation depending on the position of jaw members 110, 120 (as controlled by movable handle 40) and/or knife 184 (as controlled by trigger assembly 80), and the energization of tissue sealing plates 112, 122 (as controlled by first and second switch components 90a, 90b, respectively) and/or knife 184 (as controlled by knife activation switch 92). End effector assembly 100 is efficiently transitionable between these various different modes by controlling movable handle 40, trigger assembly 80, first and second switch components 90a, 90b, and/or knife activation switch 92. As such, end effector assembly 100 may not only be used for performing various different surgical procedures, but may also be transitioned between two or more of the above-described modes during the course of a single procedure. For example, end effector assembly 100 may be used to mechanically or electrically/electromechanically cut tissue in the open-jaw cutting mode or scissor cutting mode in order to reach underlying tissue to be sealed and/or divided. End effector assembly 100 may then be used to grasp, seal, and divide (mechanically or electrically/electromechanically) the underlying tissue. Alternatively, end effector assembly 100 may be used to grasp and seal tissue, followed by mechanically or electrically/electromechanically cutting tissue along the tissue seal via moving jaw members 110, 120 to the approximated position, advancing knife 184 between jaw members 110, 120, and cutting tissue (mechanically or electrically/electromechanically) along the tissue seal via tenting or scissor-cutting. However, end effector assembly 100 is not limited to these examples (or any specific combination of modes), but, rather, end effector assembly 100 may be transitioned between any of the above-described modes in any suitable order, i.e., end effector assembly 100 may be specifically tailored to perform a desired surgical procedure.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
an end effector assembly, including:
first and second jaw members, at least one of the jaw members movable relative to the other between a spaced-apart position and an approximated position for grasping tissue therebetween, each of the jaw members including an electrically-conductive tissue sealing plate adapted to connect to a source of energy, the tissue sealing plates selectively energizable independently of one another and configured to conduct energy therebetween and through tissue to seal tissue; and
a knife including a distal tissue-cutting surface and an upper tissue-cutting surface, the knife selectively translatable relative to the jaw members between a retracted position and an extended position wherein the knife extends between the jaw members, the knife translatable between the retracted and extended positions in each of the spaced-apart and approximated positions of the jaw members, the distal tissue-cutting surface configured for dynamic tissue cutting upon translation of the knife from the retracted position to the extended position with the jaw members disposed in the approximated position, the upper tissue-cutting surface configured for static tissue cutting when the knife is disposed in the extended position with the jaw members disposed in the spaced-apart position, the knife adapted to connect to the source of energy, the knife selectively energizable independently of the tissue sealing plates and configured to conduct energy between the knife and at least one of the tissue sealing plates and through tissue to electrically cut tissue.

2. The forceps according to claim 1, further comprising a handle assembly for selectively moving the jaw members between the spaced-apart and approximated positions.

3. The forceps according to claim 1, further comprising a trigger assembly for selectively translating the knife between the retracted and extended positions.

4. The forceps according to claim 1, further comprising a first activation switch for selectively energizing the tissue sealing plate of the first jaw member and a second activation switch for selectively energizing the tissue sealing plate of the second jaw member.

5. The forceps according to claim 1, further comprising a knife actuation switch for selectively energizing the knife.

6. The forceps according to claim 1, wherein the knife and the tissue sealing plates of the first and second jaw members are energizable to conduct energy therebetween and through tissue to electrically cut tissue when the knife is translated from the retracted position to the extended position with the jaw members disposed in the approximated position.

7. The forceps according to claim 1, wherein the knife and the tissue sealing plate of the second jaw member are energizable to conduct energy therebetween and through tissue to electrically cut tissue via tenting when the jaw members are disposed in the spaced-apart position and the knife is disposed in the extended position.

8. The forceps according to claim 1, wherein the knife and the tissue sealing plate of the first jaw member are energizable to conduct energy therebetween and through tissue to electrically cut tissue via scissor-cutting with the knife disposed in the extended position and the jaw members moving between the spaced-apart and approximated positions.

9. The forceps according to claim 1, further comprising at least one insulator disposed between the knife and the tissue sealing plates, the insulator configured to inhibit contact between the knife and the tissue sealing plates.

10. A method of surgery, comprising:
moving first and second jaw members of an end effector assembly from a spaced-apart position to an approximated position relative to one another to grasp tissue therebetween, each jaw member including an electrically-conductive tissue sealing plate adapted to connect to a source of energy;
energizing the tissue sealing plate of at least one of the first and second jaw members to seal tissue grasped between the jaw members;
moving the jaw members from the approximated position back to the spaced-apart position relative to one another;
deploying a knife between the jaw members with the jaw members disposed in the spaced-apart position;
overlaying tissue across an upper edge of the knife; and
moving the end effector assembly transversely relative to the overlayed tissue to cut the overlayed tissue via tenting.

11. The method according to claim 10, wherein the knife is adapted to connect to the source of energy and wherein moving the end effector assembly transversely relative to tissue to cut tissue via tenting includes energizing the knife to electrically cut tissue via tenting.

12. The method according to claim 11, further including activating a knife actuation switch to energize the knife.

13. The method according to claim 10, further including actuating a trigger assembly to deploy the knife between the jaw members.

14. The method according to claim 10, further including actuating a handle assembly to move the jaw members between the spaced-apart position and the approximated position.

15. The method according to claim 10, further including activating a first activation switch to energize the tissue sealing plate of the first jaw member and activating a second activation switch to energize the tissue sealing plate of the second jaw member.

16. A method of surgery, comprising:
moving first and second jaw members of an end effector assembly from a spaced-apart position to an approximated position relative to one another to grasp tissue therebetween, each jaw member including an electrically-conductive tissue sealing plate adapted to connect to a source of energy;
energizing the tissue sealing plate of at least one of the first and second jaw members to seal tissue grasped between the jaw members;
moving the jaw members from the approximated position back to the spaced-apart position relative to one another;
deploying a knife between the jaw members with the jaw members disposed in the spaced-apart position;
positioning tissue between the jaw members; and
moving the jaw members from the spaced-apart position to the approximated position to scissor-cut tissue utilizing the knife.

17. The method according to claim 16, wherein the knife is adapted to connect to the source of energy and wherein moving the jaw members from the spaced-apart position to the approximated position to scissor-cut tissue includes energizing the knife to electrically scissor-cut tissue utilizing the knife.

18. The method according to claim 17, further including activating a knife actuation switch to energize the knife.

19. The method according to claim 16, further including actuating a trigger assembly to deploy the knife between the jaw members.

20. The method according to claim 16, further including activating a first activation switch to energize the tissue sealing plate of the first jaw member and activating a second activation switch to energize the tissue sealing plate of the second jaw member.

* * * * *